(12) United States Patent
Sabbah et al.

(10) Patent No.: US 7,658,951 B2
(45) Date of Patent: Feb. 9, 2010

(54) METHOD OF IMPROVING CARDIAC FUNCTION OF A DISEASED HEART

(75) Inventors: Hani N. Sabbah, Waterford, MI (US); Viktor G. Sharov, Centennial, CO (US); Yukata Ishigai, Ichikawa (JP); Victor A. Maltsev, Parkville, MD (US)

(73) Assignee: Henry Ford Health System, Detroit, MI (US)

( * ) Notice: Subject to any disclaimer, the term of this patent is extended or adjusted under 35 U.S.C. 154(b) by 145 days.

(21) Appl. No.: 10/700,032

(22) Filed: Nov. 3, 2003

(65) Prior Publication Data
US 2004/0180043 A1 Sep. 16, 2004

Related U.S. Application Data

(63) Continuation-in-part of application No. PCT/US02/29595, filed on Sep. 18, 2002.

(60) Provisional application No. 60/323,351, filed on Sep. 19, 2001.

(51) Int. Cl.
*A61K 35/28* (2006.01)
*C12N 5/06* (2006.01)
*C12N 5/08* (2006.01)

(52) U.S. Cl. .................. 424/577; 424/520; 435/372

(58) Field of Classification Search ............... 424/93.7, 424/577
See application file for complete search history.

(56) References Cited

U.S. PATENT DOCUMENTS

| | | | |
|---|---|---|---|
| 4,666,828 A | 5/1987 | Gusella | |
| 4,683,202 A | 7/1987 | Mullis | |
| 4,801,531 A | 4/1989 | Frossard | |
| 5,192,659 A | 3/1993 | Smulson et al. | |
| 5,272,057 A | 12/1993 | Simons | |
| 6,368,636 B1 * | 4/2002 | McIntosh et al. | 424/577 |
| 6,387,369 B1 * | 5/2002 | Pittenger et al. | 424/93.7 |
| 7,097,832 B1 * | 8/2006 | Kornowski et al. | 424/93.7 |
| 2002/0123143 A1 | 9/2002 | Toma et al. | |

FOREIGN PATENT DOCUMENTS

| | | |
|---|---|---|
| EP | 1 136 083 A | 9/2001 |
| WO | 9903973 A1 | 1/1999 |
| WO | 9949015 A2 | 9/1999 |

OTHER PUBLICATIONS

Pierpaolli et al. Cellular Immunology. 1981. 57: 219-228.*
Hamano et al. Cell Transplantation. 2000, vol. 9, pp. 439-443.*
Beresford, J. N.: Osteogenic Stem Cells and the connective Stromal System of Bone and Marrow, Clin. Orthop., 240:270,1989.
Burke and Olson, "Preparation of Clone Libraries in Yeast Artificial-Chromosome Vectors" in *Methods in Enzymology*, vol. 194, "Guide to Yeast Genetics and Molecular Biology", eds. C. Guthrie and G. Fink, Academic Press, Inc., Chap. 17, pp. 251-270 (1991).
Capecchi, "Altering the genome by homologous recombination" *Science* 244:1288-1292 (1989).
Cregg JM, Vedvick TS, Raschke WC: Recent Advances in the Expression of Foreign Genes in *Pichia pastoris*, Bio/Technology 11:905-910, 1993.
Davies et al., "Targeted alterations in yeast artificial chromosomes for inter-species gene transfer", *Nucleic Acids Research*, vol. 20, No. 11, pp. 2693-2698 (1992).
Gilboa, E, Eglitis, MA, Kantoff, PW, Anderson, WF: Transfer and expression of cloned genes using retroviral vectors. BioTechniques 4(6):504-512, 1986.
Huston et al, 1991 "Protein engineering of single-chain Fv analogs and fusion proteins" in Methods in Enzymology (JJ Langone, ed.; Academic Press, New York, NY) 203:46-88.
Jackson KA, Majka SM, Wang H, Pocius J, Hartley CJ, Majesky MW, Entman ML, Michael LH, Hirschi KK, Goodell MA. Regeneration of ischemic cardiac muscle and vascular endothelium by adult stem cells. J Clin Invest Jun. 2001;107(11):1395-402.
Jakobovits et al., "Germ-line transmission and expression of a human-derived yeast artificial chromosome", *Nature*, vol. 362, pp. 255-261 (1993).
Lamb et al., "Introduction and expression of the 400 kilobase *precursor amyloid protein* gene in transgenic mice", *Nature Genetics*, vol. 5, pp. 22-29 (1993).
Maltsev VA, Rohwedel J, Hescheler J, Wobus AM: Embryonic stem cells differentiate in vitro into cardiomyocytes representing sinusnodal, artrial and ventricular cell types. *Mechanisms of Development*, 1994; 191:41-50.
Maltsev VA, Wobus AM, Rohwedel J, Bader M, Hescheler J. Cardiomyocytes differentiated in vitro from embryonic stem cells developmentally express cardiac-specific genes and ionic currents. *Circulation Research*, 1994; 75(2):233-244.

(Continued)

*Primary Examiner*—Vera Afremova

(57) ABSTRACT

A method of treating heart failure and improving cardiac function by administering stem cell products to a heart in need of treatment, whereby the stem cell products improve cardiac muscle function thereby treating heart failure and improving cardiac function. A method of enriching or regenerating damaged myocardium by administering stem cell products to damaged myocardium. Stem cell products for use in treating heart failure are also provided. A composition for enriching and regenerating damaged myocardium, the composition having stem cell products in a pharmaceutically acceptable carrier.

7 Claims, No Drawings

OTHER PUBLICATIONS

Mernaugh and Mernaugh, 1995 "An overview of phage-displayed recombinant antibodies" in Molecular Methods In Plant Pathology (RP Singh and US Singh, eds.; CRC Press Inc., Boca Raton, FL) pp. 359-365.

Orlic D, Kajstura J, Chimenti S, Jakoniuk I, Anderson SM, Li B, Pickel J, McKay R, Nadal-Ginard B, Bodine DM, Leri A, Anversa P. Bone marrow cells regenerate infracted myocardium. Nature. Apr. 5, 2001;410(6829):640-1.

Pearson and Choi, *Expression of the human b-amyloid precursor protein gene from a yeast artificial chromosome in transgenic mice.* Proc. Natl. Acad. Sci. USA, 1993. 90:10578-82.

Rothstein, "Targeting, disruption, replacement, and allele rescue: integrative DNA transformation in yeast" in *Methods in Enzymology*, vol. 194, "Guide to Yeast Genetics and Molecular Biology", eds. C. Guthrie and G. Fink, Academic Press, Inc., Chap. 19, pp. 281-301 (1991).

Sabbah HN, Stein PD, Kono T, Gheorghiade M, Levine TB, Jafri S, Hawkins ET, Goldstein S. A canine model of chronic heart failure produced by multiple sequential coronary microembolizations. *American Journal of Physiology.* 1991; 260:H1379-84.

Sabbah, HN. Apoptotic cell death in heart failure. Cardiovasc Res. 2000 45:704-712.

Schedl et al., "A yeast artificial chromosome covering the tyrosinase gene confers copy number-dependent expression in transgenic mice", *Nature*, vol. 362, pp. 258-261 (1993).

Strauss et al., "Germ line transmission of a yeast artificial chromosome spanning the murine $a_1$ (I) collagen locus", *Science*, vol. 259, pp. 1904-1907 (1993).

Wang JS, Shum-Tim D, Galipeau J, Chedrawy E, Eliopoulos N, Chiu RC. Marrow stromal cells for cellular cardiomyoplasty: feasibility and potential clinical advantages. J Thorac Cardiovasc Surg. 2000.

Aoki, M., et al. Beneficial Angiogenesis Induced by Over-Expression of Human Hepatocyte Growth Factor (HGF) in Non-Infarcted and Infarcted Myocardium: Potential Gene Therapy for Myocardial Infarction. Circulation, American Hearth Association, vol. 98, No. 17, suppl, Oct. 27, 1998, pp. I-321.

Esakof, D., et al. Intraoperative Multiplane Transesophageal Echocardiography for Guiding Direct Myocardial Gene Transfer of Vascular Endothelial Growth Factor in Patents with Refractory Angina Pectoris. Human Gene Therapy vol. 10:2307-2314 (Sep. 20, 1999).

Grant, Derrick S., et al. Scatter factor induces blood vessel formation in vivo. Proc. Natl. Acad. Sci. USA, vol. 90, pp. 1937-1941, Mar. 1993.

Harada, K., et al. Vascular endothelial growth factor administration in chronic myocardial ischemia. 1996 The American Physiological Society. H1791-1802.

Heath, Carole A., et al. Cells for tissue engineering. Trends in Biotechnology, Jan. 2000 (Vo. 18) 17-19.

Kaye, D., et al. Reduced Myocardial Nerve Growth Factor Expression in Human and Experimental Heart Failure. Circ Res. vol. 100, No. 18 suppl., 2000;86:e80-e84.

Klug, M., et al. Genetically Selected Cardiomyocytes from Differentiating Embryonic Stem Cells Form Stable Intracardiac Grafts. J. Clin. Invest. The American Society for Clinical Investigations, Inc. vol. 98, No. 1, Jul. 1996. 216-224.

Landau, C., et al. Intrapericardial basic fibroblast growth factor induces myocardial angiogenesis in a rabbit model of chronic ischemia. American Heart Journal, May 1995 924-931.

Morbidelli, L., et al. Nitric Oxide Mediates Mitogenic Effect of VEGF on Coronary Venular Endothelium. American Journal of Physiology: Heart and Circulatory Physiology, The American Physiological Society, vo. 270, No. 1, part 2, 1996, pp. H411-H415.

Tomita, S., et al. Autotransplanted Mesenchymal Stem Cells Improve Function After a Myocardial Infarction. *Circulation, American Heart Association*, vo.. 98, No. 17, suppl, Oct. 27, 1998, pp. 1-200.

* cited by examiner

METHOD OF IMPROVING CARDIAC FUNCTION OF A DISEASED HEART

CROSS-REFERENCE TO RELATED APPLICATIONS

This Continuation-In-Part Patent Application claims priority to PCT/US02/29595, filed Sep. 18, 2002, which claims the benefit of priority under 35 U.S.C. Section 119(e) of U.S. Provisional Patent Application No. 60/323,351, filed Sep. 19, 2001, both of which are incorporated herein by reference.

BACKGROUND OF THE INVENTION

1. Technical Field

The present invention relates to the field of heart failure treatments. More specifically, the present invention relates to the use of transplanting cell populations, specifically stem cells, for the treatment of heart failure.

2. Description of the Related Art

Diseases of the cardiovascular system are a leading worldwide cause of mortality and morbidity. Heart failure has been increasing in prevalence. Heart failure is characterized by an inability of the heart to deliver sufficient blood to the various organs of the body. Current estimates indicate that over 5 million Americans carry the diagnosis of heart failure with nearly 500,000 new cases diagnosed each year and 250,000 deaths per year attributed to this disease. Despite significant therapeutic accomplishments in the past two decades, heart failure continues to increase in incidence reaching epidemic proportions and presenting a major economic burden in developed countries.

Heart failure is a clinical syndrome characterized by distinctive symptoms and signs resulting from disturbances in cardiac output or from increased venous pressure. Moreover, heart failure is a progressive disorder whereby the function of the heart continues to deteriorate over time despite the absence of adverse events. The result of heart failure is inadequate cardiac output.

Generally, there are two types of heart failure. Right heart failure is the inability of the right side of the heart to pump venous blood into pulmonary circulation. Thus, a back-up of fluid in the body occurs and results in swelling and edema. Left heart failure is the inability of the left side of the heart to pump blood into systemic circulation. Back-up behind the left ventricle then causes accumulation of fluid in the lungs.

The main resulting effect of heart failure is fluid congestion. If the heart becomes less efficient as a pump, the body attempts to compensate for it by using hormones and neural signals to increase blood volume.

Heart failure has numerous causes. For example, disease of heart tissue results in myocardial cells that no longer function. Thus, progression of left ventricular dysfunction has been attributed, in part, to ongoing loss of these cardiomyocytes.

There have been numerous methods of treating and preventing heart failure. For example, stem cells have been used to regenerate cardiac cells in acute cardiac ischemia and/or infarction or injury in animal models. In one particular example, viable marrow stromal cells isolated from donor leg bones were culture-expanded, labeled, and then injected into the myocardium of isogenic adult rat recipients. After harvesting the hearts from 4 days to 12 weeks after implantation, the implantation sites were examined and it was found that implanted stromal cells show the growth potential in a myocardial environment (Wang, et. al.).

Cardiomyocytes also have been shown to differentiate in vitro from pluripotent embryonic stem (ES) cells of line D3. The cells differentiated via embryo-like aggregates (embryoid bodies) that were characterized by the whole-cell patch-clamp technique, morphology, and gene expression analogy during the entire differentiation period (Maltsev, et. al., 1994). However, the cells must be differentiated in vitro prior to administration. Additionally, pluripotent mouse ES cells were able to differentiate, in vitro, into cardiomyocytes expressing major features of mammalian heart (Maltsev, et. al., 1993).

Stem cells, regardless of their origin (embryonic, bone marrow, skeletal muscle, etc), have the potential to differentiate into various, if not all, cell types of the body. Stem cells are able to differentiate into functional cardiac myocytes. Thus, the development of stem cell-based therapies for treating heart failure has many advantages over existing therapies.

There is a need for a method of improving and/or restoring cardiac function in patients with heart failure through the use of cardiac transplantation of stem cells. Additionally, there is a need for a method of increasing the performance of the heart through implantation and population of failing myocardium with stem cells.

SUMMARY OF THE INVENTION

In accordance with the present invention, there is provided a method of treating heart failure and improving cardiac function by administering stem cell products to a heart in need of treatment, whereby the stem cell products improve cardiac muscle function thereby treating heart failure and improving cardiac function. A method of enriching or regenerating damaged myocardium by administering stem cell products to damaged myocardium. Stem cell products for use in treating heart failure are also provided. A composition for enriching and regenerating damaged myocardium, the composition having stem cell products in a pharmaceutically acceptable carrier.

DESCRIPTION OF THE INVENTION

Generally, the present invention provides a method and composition for the treatment of heart failure. More specifically, the present invention provides a method and composition for improving and/or restoring cardiac function by administering a composition containing stem cells to a patient in need of treatment.

The term "stem cell" as used herein is meant to include but is not limited to, a generalized mother cell whose descendants differentiate into various cell types. Stem cells have various origins including, but not limited to, embryo, bone marrow, liver, fat tissue, and other stem cell origins known to those of skill in the art. These stem cells are placed into the desired areas as they naturally occur. While the prior art techniques utilize various genetic engineering methods including, but not limited to, transfection, deletion, and the like in order to increase their likelihood of survival or for any other desired purpose, the stem cells of the present invention are able to function effectively without requiring genetic engineering.

The purpose of the present invention is to utilize stem cells, supernatant from stem cells, the secretions resulting from the interaction of stem cells and other cells (e.g., stem cell products), or compounds that increase the amount of secretions present at a site, for treating heart failure. These secretions include, but are not limited to, an array of growth, trophic, and angiogenesis factors including, but not limited to, hypoxia-inducible factor-1-alpha. The method of the present invention promotes an improved outcome from cardiac injury by augmenting or causing the regeneration of cardiac muscle cells.

Stem cells are capable of self-regeneration when administered to a human subject in vivo, and can become lineage-restricted progenitors, which further differentiate and expand into specific lineages. Further, unless indicated otherwise, "stem cells" refers to human marrow stromal cells. Human marrow stromal cells are found in the bone marrow. Bone marrow is soft tissue occupying medullary cavities of long bones, some haversian canals, and spaces between trabeculae of cancellous or spongy bone. Bone marrow is of two types: red, which is found in all bones in early life and in restricted locations in adulthood (i.e., in the spongy bone) and is concerned with the production of blood cells (i.e. hematopoiesis) and hemoglobin (thus, the red color); and yellow, which consists largely of fat cells (thus, the yellow color) and connective tissue.

As a whole, bone marrow is a complex tissue comprised of hematopoietic stem cells, red and white blood cells and their precursors, mesenchymal stem cells, stromal cells and their precursors, and a group of cells including fibroblasts, reticulocytes, adipocytes, and endothelial cells that form a connective tissue network called "stroma." Cells from the stroma morphologically regulate the differentiation of hematopoietic cells through direct interaction via cell surface proteins and the secretion of growth factors and are involved in the foundation and support of the bone structure. Studies using animal models have suggested that bone marrow contains "pre-stromal" cells that have the capacity to differentiate into cartilage, bone, and other connective tissue cells. (Beresford, J. N.: Osteogenic Stem Cells and the Stromal System of Bone and Marrow, Clin. Orthop., 240:270, 1989). Recent evidence indicates that these cells, called pluripotent stromal stem cells or mesenchymal stem cells, have the ability to generate into several different types of cell lines (i.e., osteocytes, chondrocytes, adipocytes, etc.) upon activation. The mesenchymal stem cells are present in the tissue in very minute amounts with a wide variety of other cells (i.e., erythrocytes, platelets, neutrophils, lymphocytes, monocytes, eosinophils, basophils, adipocytes, etc.), and in an inverse relationship with age, the mesenchymal stem cells are capable of differentiating into an assortment of connective tissues depending upon the influence of a number of bioactive factors.

The terms "stem cell" or "pluripotent" stem cell are used interchangeably to mean a stem cell having (1) the ability to give rise to progeny in all defined hematopoietic lineages, and (2) the capability to fully reconstitute a seriously immuno-compromised host in all blood cell types and their progeny, including the pluripotent hematopoietic stem cell, by self-renewal.

The terms "enrich" or "enrichment" as used herein are meant to include, but are not limited to, a process of making rich or richer by the addition or increase of some desirable quality or quantity of substance. In the present invention, enrichment occurs by the addition or increase of more functional cardiac cells within or around the myocardium. The desired therapeutic effect of the present invention is the ultimate enrichment of functional cardiac cells in situ.

The terms "repopulate" or "repopulating" as used herein are meant to include, but are not limited to, the addition or replenishment of cardiac cells within or around the myocardium. These additionally reinforce the activity of currently functioning cells. Thus, replacement and/or reinforcement of existing cardiac cells occurs.

The term "cell therapy" as used herein is meant to include but is not limited to, the administration of stem cells and their products as defined above.

The term "injury" as used herein is intended to include, but is not limited to, physical or biological injuries including genetic disorders, diseases, and age onset disorders that occur in the heart. The stem cells operate to increase cardiac function and/or treat heart failure by differentiating into functional cardiac muscle cells, thereby treating the injury.

It has become abundantly clear that one mechanism for the deterioration of function in heart failure of any etiology is due, in part, to the ongoing death of heart muscle cells (Sabbah, 2000). The solution to this problem is to enrich and/or repopulate the myocardium with new functional cardiac cells that take the place of lost cells or provide additional reinforcement of the currently functioning cardiac cells, thereby improving the pumping function of the failing heart.

The production of trophic factors, growth factors, and angiogenic factors is typically an expensive and difficult process. The method and composition of the present invention provide an inexpensive and simple method of producing pure trophic factors, growth factors, and other related factors or products. These factors/products can be used for treatment of patients. For example, the factors can be used for inducing angiogenesis and enhancing function and repair of tissues both in vivo and in vitro. It is, therefore, beneficial to determine that bone marrow stromal cells can be employed as cellular factories for producing and secreting trophic, growth, and angiogenic factors. These factors can include, but are not limited to, VEGF, HGF, BDNF, NGF, BDNF, stat5, CNTF, NGF, bFGF, hypoxia-inducible factor-1-alpha, fibroblast growth factor, pharmacologic agents including immunosuppressants such as cyclosporin A, anti-inflammation agents such as dexamethasone, anti-angiogenic factors, acidic and basic fibroblast growth factors, vascular endothelial growth factor, hif-1, epidermal growth factor, transforming growth factor-alpha and beta, platelet-derived endothelial growth factor, platelet-derived growth factor, tumor necrosis factor alpha., hepatocyte growth factor and insulin-like growth factor; growth factors; cell cycle inhibitors including CDK inhibitors; anti-restenosis agents, including p15, p16, p18, p19, p21, p27, p53, p57, Rb, nFkB and E2F decoys, thymidine kinase ("TK"), anti-glial agents, and anti-mitotic factors etc. Additionally, the present invention provides compounds that cause the stem cell factors/products to be expressed.

The present invention is based on the use of cell therapy, or stem cell products to treat disease. Although stem cells have different origins (embryo, bone marrow, liver, fat tissue, etc.), the important common characteristic is that stem cells have the potential to differentiate into various, if not all, cell types of the body. As previously mentioned, stem cells have been shown to be able to differentiate into cardiac muscle cells, when cultured properly prior to administration. (Maltsev et al., 1993; 1994)

The present invention treats heart failure and improves and/or restores cardiac function. Cardiac function is increased by enriching and/or repopulating cardiac cells, particularly contractile units, through transplanted stem cells that differentiate into cardiac cells. Alternatively, cardiac function can be increased by administering stem cell factor/products to a location in need of such treatment. Thus, the increase of contractile units increases the function of the heart. Additionally, the stem cells or stem cell factors/products can be also responsible for the release of various substances such as trophic factors, which, for example, induce angiogenesis (increase of the number of blood vessels) in order to increase cardiac function and/or treat heart failure. Therefore, the stem cells operate to increase cardiac function and/or treat heart failure through various mechanisms other than just differentiating into functional cardiac muscle cells.

More specifically, the present invention provides a method and composition for treating heart failure. The method includes the step of administering, to a patient, stem cells or stem cell factor/products. The stem cells have not been previously differentiated or otherwise treated. The stem cells are merely harvested, expanded if necessary, and administered. Previously, researchers did not believe that it was sufficient to merely introduce the stem cells. Instead, treatment previously involved complicated procedures for genetically engineering the stem cells or involved the administration of additional compounds in conjunction with the stem cells. The present invention differs from the prior art because these additional steps are not required. The present invention simplifies the entire procedure by only requiring the administration of stem cells without any genetic engineering or additional compounds.

The stem cells or products thereof can be administered at the specific location of the injury. Alternatively, the stem cells can be placed at general sites within the patient, for example, the stem cells and stem cell products can be administered intravenously and/or intracoronary. The stem cells then migrate to site of injury. Additionally, the stem cells can product products that enhance cellular function locally (e.g., at the site of administration) and away from the cells (e.g., the products can effect function at a site distant from the site of administration). In other words, the stem cell products can affect cardiac function regardless of the location of administration. This enables the stem cells or stem cell products to be administered at any location in the patient.

The general method of transplanting stem cells into the myocardium occurs by the following procedure. The stem cells are administered to the patient. The administration can be subcutaneously, parenterally including intravenous, intraarterially, intramuscularly, intraperitoneally, and intranasally as well as intrathecally and infusion techniques.

The human mesenchymal stem cells can be obtained from a number of different sources, including plugs of femoral head cancellous bone pieces, obtained from patients with degenerative joint disease during hip or knee replacement surgery, and from aspirated marrow obtained from normal donors and oncology patients who have marrow harvested for future bone marrow transplantation. Although the harvested marrow was prepared for cell culture separation by a number of different mechanical isolation processes depending upon the source of the harvested marrow (i.e., the presence of bone chips, peripheral blood, etc.), the critical step involved in the isolation processes was the use of a specially prepared medium that contained agents that allowed for not only mesenchymal stem cell growth without differentiation, but also for the direct adherence of only the mesenchymal stem cells to the plastic or glass surface area of the culture dish. By producing a medium that allowed for the selective attachment of the desired mesenchymal stem cells that were present in the marrow samples in very minute amounts, it was possible to separate the mesenchymal stem cells from the other cells (i.e., red and white blood cells, other differentiated mesenchymal cells, etc.) present in the bone marrow. Optionally, the medium can be enriched by exposing the media to hypoxia. The enrichment enables the stem cells and stem cells products to be used as a treatment.

As indicated above, the complete medium can be utilized in a number of different isolation processes depending upon the specific type of initial harvesting processes used in order to prepare the harvested bone marrow for cell culture separation. When plugs of cancellous bone marrow were utilized, the marrow was added to the complete medium and vortexed to form a dispersion that was then centrifuged to separate the marrow cells from bone pieces, etc. The marrow cells (consisting predominantly of red and white blood cells, and a very minute amount of mesenchymal stem cells, etc.) were then dissociated into single cells by passing the complete medium containing the marrow cells through syringes fitted with a series of 16, 18, and 20 gauge needles. The advantage of the mechanical separation process, over any enzymatic separation process, is that the mechanical process produces little cellular change while an enzymatic process produces cellular damage particularly to the protein binding sites needed for culture adherence and selective separation and/or to the protein sites needed for the production of monoclonal antibodies specific for said mesenchymal stem cells. The single cell suspension (made up of approximately $50\text{-}100 \times 10^6$ nucleated cells) was then subsequently plated in 100 mm dishes for the purpose of selectively separating and/or isolating the mesenchymal stem cells from the remaining cells found in the suspension.

When aspirated marrow was utilized as the source of the human mesenchymal stem cells, the marrow stem cells (that contained little or no bone chips but a great deal of blood) were added to the complete medium and fractionated with Percoll (Sigma, St. Louis, Mo.) gradients more particularly described below. The Percoll gradients separated a large percentage of the red blood cells and the mononucleate hematopoietic cells from the low-density platelet fraction that contained the marrow-derived mesenchymal stem cells. The platelet fraction, which contained approximately $30\text{-}50 \times 10^6$ cells, was made up of an undetermined amount of platelet cells, $30\text{-}50 \times 10^6$ nucleated cells, and only about 50-500 mesenchymal stem cells depending upon the age of the marrow donor. The low-density platelet fraction was then plated in the Petri dish for selective separation based upon cell adherence.

The marrow cells obtained from either the cancellous bone or iliac aspirate (i.e. the primary cultures) were grown in complete medium and allowed to adhere to the surface of the Petri dishes for one to seven days according to the conditions set forth below. Since no increase in cell attachment was observed after the third day, three days was chosen as the standard length of time at which the non-adherent cells were removed from the cultures by replacing the original complete medium with fresh complete medium. Subsequent medium changes were performed every four days until the culture dishes became confluent, which normally required 14 to 21 days. This represented $10^3$ to $10^4$-fold increase in undifferentiated human mesenchymal stem cells.

The cells were then detached from the culture dishes utilizing a releasing agent such as trypsin with EDTA (ethylene diaminetetra-acetic acid) (0.25% trysin, 1 mM EDTA (1×), Gibco, Grand Island, N.Y.) or a chelating agent such as EGTA (ethylene glycol-bis-(2-amino ethyl ether) N,N'-tetraacetic acid, Sigma Chemical Co., St. Louis, Mo.). The advantage produced through the use of a chelating agent over trypsin was that trypsin can cleave off a number of the binding proteins of the mesenchymal stem cells. Since these binding proteins contain recognition sites, when monoclonal antibodies were produced, a chelating agent such as EGTA as opposed to trypsin, was utilized as the releasing agent. The releasing agent was then inactivated and the detached, cultured, and undifferentiated mesenchymal stem cells were washed with complete medium for subsequent use.

The dosage of the mesenchymal stem cells varies within wide limits and is fitted to the individual requirements in each particular case. In general, in the case of parenteral administration, it is customary to administer from about 0.01 to about 5 million cells per kilogram of recipient body weight. The number of cells used depends on the weight and condition of the recipient, the number of or frequency of administrations, and other variables known to those of skill in the art. The mesenchymal stem cells can be administered by a route that is suitable for the tissue, organ, or cells to be transplanted. They can be administered systemically, i.e., parenterally by intravenous injection, or can be targeted to a particular tissue or organ, such as bone marrow. The human mesenchymal stem cells can be administered via subcutaneous implantation of cells or by injection into connective tissue, e.g., muscle.

The stem cells can be suspended in an appropriate diluent, at a concentration of from about 0.01 to about $5\times10^6$ cells/ml. Suitable excipients for injection solutions are those that are biologically and physiologically compatible with the cells and with the recipient, such as buffered saline solution or other suitable excipients. The composition for administration must be formulated, produced and stored according to standard methods complying with proper sterility and stability.

Although the invention is not limited thereto, mesenchymal stem cells can be isolated, preferably from bone marrow, purified, and expanded in culture, i.e., in vitro, to obtain sufficient numbers of cells for use in the methods described herein. Mesenchymal stem cells, the formative pluripotent blast cells found in the bone, are normally present at very low frequencies in bone marrow (1:100,000) and other mesenchymal tissues. See, Caplan and Haynesworth, U.S. Pat. No. 5,486,359. Gene transduction of mesenchymal stem cells is disclosed in Gerson et al U.S. Pat. No. 5,591,625. Unless otherwise stated, genetic manipulations are performed as described in Sambrook and Maniatis, MOLECULAR CLONING: A LABORATORY MANUAL, 2nd Ed.; Cold Spring Harbor Laboratory Press, Cold Spring Harbor, N.Y. (1989).

In one embodiment of the present invention, a reproducible canine chronic heart failure (HF) model that mimics many properties of heart failure in humans including left ventricular (LV) systolic and diastolic dysfunction (Sabbah et al., 1991) is demonstrated. In a study using this canine model of HF, regional function of the failing left ventricle improves dramatically one month after transplantation of autologous bone marrow stem cells into that region of the ventricle, wherein transplantation is defined as placing the stem cells within the site of the injury.

One method of transplanting stem cells into the myocardium occurs by the following procedure. Additionally, variations on this general procedure can be derived from the prior art references attached hereto and incorporated herein by reference in their entirety. First, two weeks prior to cell transplantation, bone marrow is aspirated from the femur of a dog with heart failure. Stem cells from the bone marrow are cultured and allowed to proliferate for a period of two weeks. Two weeks after bone marrow aspiration, the same dog undergoes open chest surgery. The pericardium is opened and a total of thirteen injections of stem cells are made directly into the anterior wall of the left ventricle. Each injection contained approximately 350,000 cells. The chest is then closed and the animal allowed to recover. Left ventricular function is assessed before and one month after cell transplantation compared to baseline.

The therapy of the invention can be provided by several routes of administration, including the following. First, intracardiac muscle injection, which avoids the need for an open surgical procedure, can be used where the stem cells are in an injectible liquid suspension preparation or where they are in a biocompatible medium that is injectible in liquid form and becomes semi-solid at the site of damaged myocardium. A conventional intracardiac syringe or a controllable arthroscopic delivery device can be used so long as the needle lumen or bore is of sufficient diameter (e.g. 30 gauge or larger) that shear forces cannot damage the stem cells. The injectible liquid suspension stem cell preparations can be also administered intravenously, either by continuous drip or as a bolus. During open surgical procedures involving direct physical access to the heart, any other forms of stem cell delivery preparations known to those of skill in the art are available options.

A representative example of a dose range is a volume of about 20 to about 50 µl of injectible suspension containing $10^{-40}\times10^6$ MSCs/ml. The concentration of cells per unit volume, whether the carrier medium is liquid or solid, remains within substantially the same range. The amount of stem cells delivered is usually greater when a solid, "patch" type application is made during an open procedure, but follow-up therapy by injection can be also performed. The frequency and duration of therapy does, however, vary depending on the degree (percentage) of tissue involvement, as already described (e.g. 5-40% left ventricular mass).

In cases of tissue involvement in the range of 5 to 10% severity level, it is possible to treat with as little as a single administration of one million stem cells in 20 to 50 µl of injection preparation. The injection medium can be any pharmaceutically acceptable isotonic liquid. Examples include phosphate buffered saline (PBS), culture media such as DMEM (preferably serum-free), physiological saline, or 5% dextrose in water (D5 W).

In cases tissue involvement in a range of around 20% severity level, multiple injections of 20 to 50 µl ($10^{-40}\times10^6$ MSCs/ml) are envisioned. Follow-up therapy can involve additional dosings.

In very severe cases, e.g., in a range around 40% tissue involvement severity level, multiple equivalent doses for a more extended duration with long-term (up to several months) maintenance dose aftercare may be indicated.

The present invention is advantageous over all currently existing treatments. For example, treatment of heart failure is currently based primarily on the use of drugs that interfere with neurohumoral systems. Additionally, surgical treatments exist that include heart transplantation as well as the use of ventricular or bi-ventricular assisting devices. The advantage offered by the present invention is the ability to treat heart failure by directly addressing the primary cause of the disease, namely, loss of contractile units. Repopulation of the myocardium with stem cells that differentiate into contractile units that contribute to the overall function of the failing heart, therefore, is novel and goes to the center of the problem. Other advantages include (1) absence of side effects that are often associated with the use of pharmacological therapy, (2) absence of immune rejection that plagues heart transplantation or other organ transplants, and (3) the ability to increase the trophic factors created by the stem cells.

The present invention has the potential to replace many current surgical therapies and possibly even pharmacological therapies. Devices currently exist that allow delivery of stem cells to the failing heart using catheter-based approaches, thus eliminating the need for open chest surgery. Additionally, the present invention is applicable in both the human and veterinary medical setting.

The following information and the information disclosed in the attached references, which are incorporated by reference in their entireties, describe various methods and materials that can be utilized with the present invention. While specific embodiments are disclosed herein, they are not exhaustive and can include other suitable designs that vary in design and methodologies known to those of skill in the art. Basically, any differing designs, methods, structures, and materials known to those skilled in the art can be utilized without departing from the spirit of the present invention.

EXAMPLES

Methods:

General methods in molecular biology: Standard molecular biology techniques known in the art and not specifically described were generally followed as in Sambrook et al., *Molecular Cloning: A Laboratory Manual*, Cold Spring Harbor Laboratory Press, New York (1989), and in Ausubel et al., *Current Protocols in Molecular Biology*, John Wiley and Sons, Baltimore, Md. (1989) and in Perbal, *A Practical Guide to Molecular Cloning*, John Wiley & Sons, New York (1988), and in Watson et al., *Recombinant DNA*, Scientific American Books, New York and in Birren et al (eds.) *Genome Analysis: A Laboratory Manual Series*, Vols. 1-4 Cold Spring Harbor Laboratory Press, New York (1998) and methodology as set forth in U.S. Pat. Nos. 4,666,828; 4,683,202; 4,801,531; 5,192,659 and 5,272,057 and incorporated herein by reference. Polymerase chain reaction (PCR) was carried out generally as in *PCR Protocols: A Guide To Methods And Applications*, Academic Press, San Diego, Calif. (1990). In-situ (In-cell) PCR in combination with Flow Cytometry can be used for detection of cells containing specific DNA and mRNA sequences (Testoni et al, 1996, Blood 87:3822.)

Example 1

Hypoxia Stimulates Production of STAT-3 in Cultured Bone Marrow Cells

Bone marrow stem cell (BMSC) transplantation has been shown to regenerate infarcted myocardium (M) and improve LV function. The hypothesis that exposure of BMSC to hypoxia (HX), a stress factor typically present in injured and/failing M, activates STAT-3, a protein that functions as activator of transcription that has been implicated in tissue regeneration and angiogenesis is tested herein.

Methods:

BMSC of adult dogs were cultured using Iscove's modified Dulbecco's medium. HX was produced by placing BMSC in an air-tight incubator where room air was replaced by 95% $N_2$/5% $CO_2$. BMSC incubated under normoxic (95% room air/5% $CO_2$) condition (NX) served as control. BMSC were harvested at baseline and after one hour of exposure to HX or NX. Cells were homogenized and Western blots performed using a polyclonal STAT-3 antibody. Bands were quantified in densitometric units.

Results:

Exposure of BMSC to one hour of HX resulted in a six-fold increase in STAT-3 expression compared to BMSC exposed to NX (25.1±23 vs. 3.9±0.1, P<0.001). Microscopic examination of the BMSC after one hour of HX showed substantial increase of cytoplasmic projections suggestive of increased BMSC activity.

Conclusions:

Exposure of BMSC to hypoxia leads to a marked up regulation of the transcription activator STAT-3. Hypoxia is therefore one physiologic stimulus that drives BMSC differentiation in vivo.

Example 2

Canine Model for Use in Analyzing Benefit of Stem Cell Therapy

A canine model of chronic heart failure was produced by multiple sequential intracoronary embolizations with microspheres. Twenty closed-chest dogs underwent three to nine intracoronary embolizations performed one to three weeks apart. Embolizations were discontinued when left ventricular (LV) ejection fraction was <35%. LV ejection fraction was 64±2% at baseline and decreased to 21±1% at three months after the last embolization (P<0.001). During the same period, LV end-diastolic pressure increased from 6±1 to 22±3 mmHg (P<0.001); LV end-diastolic volume increased from 64±3 to 101±6 ml (P<0.001), and cardiac output decreased from 2.9±0.2 to 2.3±0.1 l/min (P<0.01). These changes were accompanied by significant reductions of peak LV+dP/dt and peak LV−dP/dt and significant increases of pulmonary artery wedge pressure and systemic vascular resistance. Plasma norepinephrine increased from 332±17 pg/ml at baseline to 791±131 pg/ml at three months after the last embolization (P<0.01); plasma levels of atrial natriuretic factor increased from 12.7±10.0 to 28.8±8.6 pmol I (P<0.01), whereas plasma rennin activity remained unchanged. Gross and microscopic postmortem examination showed patchy myocardial fibrosis and LV hypertrophy. Multiple intracoronary embolizations with microspheres, separated in time, can lead to chronic heart failure in dogs. The preparation is stable and reproducible and manifests many of the sequelae of heart failure that result form loss of contractile myocardium.

Studies were performed on 20 healthy mongrel dogs weighing between 21 and 35 kg. The protocol was approved by the Henry Ford Hospital Care of Experimental Animals Committee. Each animal underwent a series of cardiac catheterizations over a period of six to nine months to perform the coronary embolizations and subsequently to evaluate the cardiac status. All cardiac catheterizations were performed under general anesthesia and sterile conditions. Dogs were anesthetized with an intravenous injection of 0.1 mg/kg Innovar-Vet (droperidol 2.0 mg/kg and fentanyl citrate 0.04 mg/kg) followed by an intravenous injection of 7.5 mg/kg of pentobarbital sodium. This anesthetic regimen was effective in preventing the tachycardia, hypertension, and myocardial depression often seen in dogs anesthetized with pentobarbital alone. Left and right heart catheterization was performed through a femoral or a carotid arteriotomy and venotomy. At the completion of the procedure, the arteriotomy was repaired and the vein ligated. Each dog underwent an average of ten catheterization procedures (range 8-12) during which time both the left and right femoral arteries were entered four times each and the left and right carotid arteries once or twice each.

Chronic heart failure mediated by loss of contractile myocardium can be effectively produced in dogs by graded sequential intracoronary embolizations with microspheres. The model manifests many of the sequelae of heart failure including marked depression of LV systolic and diastolic function, LV dilation and hypertrophy, reduced cardiac output, development of mitral regurgitation, and elevation of systemic vascular resistance. The depression of LV function is accompanied by activation of the sympathetic nervous system and by increased secretion of ANF.

The approach used in the present study to develop chronic heart failure in the dog is different from previous attempts in which a single intracoronary injection of microspheres was utilized to induce lasting myocardial dysfunction (Franciosa et al., 1980; Palmer et al., 1971; Smiseth et al., 1983; Weber et al., 1972). Franciosa et al. (Franciosa et al., 1980) injected 400 to 600 μm glass beads into the left circumflex coronary artery of dogs to produce chronic LV dysfunction. This approach resulted in an early mortality of nearly 50%. Weber et al. (Weber et al., 1972) produced chronic LV dysfunction in calves by slowly injection 6 to 14 μm latex microspheres into the left main coronary artery over a period of four to six hours.

The early mortality was only 22% (Weber et al., 1972), but the ensuing LV dysfunction in surviving animals was only moderate. More recently, Smiseth et al. (Smiseth et al., 1983) used a single intracoronary injection of 50-μm microspheres in dogs to produce acute severe depression of LV function. In their study, the mortality rate was nearly 70%. Dogs that survived for two to four weeks after the embolization showed near complete restoration of LV function despite some morphological signs of progressive myocardial damage (Smiseth et al., 1983). The above studies suggest that a single myocardial insult sufficient to produce lasting LV dysfunction is likely to be lethal, whereas a single insult of a lesser magnitude is likely to be effectively compensated for within a few days. The approach used in the present study, namely multiple coronary embolizations separated in time, cumulatively results in myocardial lesions sufficient to produce chronic heart failure and that would have been lethal if established in a single intervention.

An important feature of the present model of heart failure is the observation of a lack of recovery of LV function once coronary embolizations were discontinued. Partial recovery of LV function after acute coronary occlusion has been described in dogs (Theroux et al., 1976) and can be accounted for, in part, by the presence of a substantial collateral circulation. Restoration of LV function can also be due to subsequent recovery of reversibly injured cells suggested by Lindal et al. (Lindal et al., 1986). In the model of chronic heart failure, it is likely that multiple embolization, separated in time, gradually exhausts the compensatory mechanisms available to the myocardium to counteract the loss of viable tissue and, therefore, leads to a sustained depression of cardiac function.

Observations of increased plasma norepinephrine concentration during the evolution of heart failure are comparable to those of patients with congestive heart failure (Curtiss et al., 1987; Levine et al., 1982). Even though plasma norepinephrine concentration increased substantially in the present model, PRA remained within normal limits throughout the course of evolving heart failure. In patients with heart failure, PRA was found to vary markedly and was normal, subnormal, or elevated (Curtiss et al., 1987; Levine et al., 1982). It is notable that in the present study, no relationship was found between plasma norepinephrine concentration and PRA, a finding that is also consistent with observations made in patients with heart failure (Curtiss et al., 1987). In contrast, studies in dogs in which heart failure was produced by rapid ventricular pacing showed an increase of PRA in conjunction with increased levels of plasma norepinephrine (Armstrong et al., 1986). The basis for this disparity does not reflect the differences in the etiology of heart failure in these two animal models. It is also possible that in the present model, normal levels of PRA indicate a state of adequate compensation (Watkins et al., 1976). Because ANF can diminish the release of rennin, the absence of elevation of PRA in the present dog model is, in part related to increased secretion of ANF, which is also seen in patients with chronic heart failure (Gottlieb et al., 1989).

In conclusion, the present study demonstrated that multiple intracoronary embolizations with microspheres, separated in time, can lead to chronic heart failure in dogs. The preparation is stable, reproducible, and is associated with an acceptable mortality. In addition to the marked and sustained depression of LV function, this model manifests many of the sequelae of heart failure including LV hypertrophy and dilatation, increased LV filling pressure and systemic vascular resistance, activation of the sympathetic nervous system, and increased secretion of ANF. The model is well suited for studying the pathophysiology of heart failure mediated by loss of contractile myocardium and for the evaluation of the efficacy of pharmacological and other therapeutic interventions.

Example 3

Transplantation of bone marrow stem cells (BMSC) into infracted or failing myocardium has been shown to stimulate angiogenesis and improve LV function. The mechanisms through which engrafted BMSC elicit the in-vivo beneficial effects on injured and/or failing myocardium is not fully understood. It is shown herein that hypoxia (HX) of cardiomyocytes occurs in heart failure (HF) and in infarct border regions and is mediated, in part, by the presence of interstitial fibrosis, reduced capillary density, and increased oxygen diffusion distance. The beneficial effect of BMSC transplantation into infracted or failing myocardium is, at least partially, triggered by response of BMSC to hypoxic environment of diseased myocardium.

Methods:

BMSC obtained from adult mongrel dogs were cultured using Iscove's modified Dulbecco's media. HX was produced by placing BMSC in an airtight incubator where room air was replaced by 95% $N_2$/5% $CO_2$. BMSC incubated under normoxic (95% Air/5% $CO_2$) condition (NX) served as a control. BMSC were harvested after one hour of exposure to HX or NX. The media left after harvesting of BMSC was used for another set of experiments. Fresh set of BMSC was incubated in the media left after HX experiment (HX preconditioned media) for two weeks. Incubation of BMSC in the media left after NX experiment was used as a control. In all sets of experiments, expression of HIF-1α, STAT-3, VEGF, and Sarcomeric-α-actinin was measured in homogenized BMSC as well as in the media using a specific antibody. An expression of HIF-1α and STAT-3 was also measured in cardiomyocytes isolated from normal and failing hearts. Bands from Western blots were quantified in densitometric units.

Results:

Compared to NX, exposure of BMSC to HX increased the expression of HIF-1α (2.6±0.44 vs. 21.6±1.27, p<0.0001) and Stat-3 (7.92±0.92 vs. 11.28±0.84, p<0.0001) within the cells compared to culturing of BMSC in NX precondition media. Culturing of BMSC in HX preconditioned media also increased the expression of HIF-1α (2.6±0.44 vs. 16.1±0.54, p<0.0001) and Stat-3 (7.92±0.92 vs. 10.8±1.57, p<0.0001). In addition, expression of VEGF and Sarcomeric-α-actinin within the cells was also increased (5.9±0.92 vs. 17.35±1.57, p<0.0001; 8.72+0.62 vs. 12.97±0.48, p<0.0001) correspondingly. In the media, expression of HIF-1α was significantly higher after one hour of exposure to HX compared to NX (4.45±0.82 vs. 16.82±1.59, p<0.0001). STAT-3, VEGF and Sarcomeric-α-actinin was not detected in the media. Expression of HIF-1α, STAT-3 was lower in cardiomyocytes isolated from failing heart compared to normal cardiomyocytes by two fold.

Conclusion:

Results of this study indicate that culturing of BMCS in HX preconditioned media mimics the results obtained from an experiment with one hour HX of BMSC in terms of expression of HIF-1α and Stat-3. The culturing of BMSC in HX preconditioned media is even more effective compared with direct HX of BMSC in terms of VEGF and Sarcomeric-α-actinin expression, which is increased after culturing of BMSC in HX preconditioned media and remained unchanged after direct hypoxia. The elaboration of HIF-1α into the HX BMSC environment can, in part, explain an activity of HX BMSC preconditioned media. The improvement in cardiac function seen following BMSC transplantation in the setting of HF and/or infarction is due, in part, to the elaboration of HIF-1α into hypoxic environment which can activate the transcription of many genes, such as STAT-3, VEGF, Sarcomeric α-actinin, etc., required for angiogenesis and for cellular responses to chronic hypoxia. The latter is important because hypoxic failing cardiomyocytes fail to perform an adequate response to chronic hypoxia due to decreased expression of HIF-1α and STAT-3.

Based upon the above findings, it can be concluded that hypoxia preconditioned BMSC media represents a potential drug for treatment of the failing heart: a) to stimulate internal blood flow circulating stem sells differentiation for replacement of the cell lost during the disease by triggering in those cells up-regulation of STAT-3, VEGF, Sarcomeric-α-actinin and HIF-1α; b) to stimulate angiogenesis by providing HIF-1α into environment; and c) to help diseased failing cardiomyocytes with down-regulated HIF-1α and STAT-3 to fight chronic hypoxia by providing additional HIF-1α into the environment.

Throughout this application, various publications, including United States patents, are referenced by author and year, and patents by number. Full citations for the publications are listed below. The disclosures of these publications and patents in their entireties are hereby incorporated by reference into this application in order to more fully describe the state of the art to which this invention pertains.

The invention has been described in an illustrative manner, and it is to be understood that the terminology that has been used is intended to be in the nature of words of description rather than of limitation.

Obviously, many modifications and variations of the present invention are possible in light of the above teachings. It is, therefore, to be understood that within the scope of the described invention, the invention can be practiced otherwise than as specifically described.

REFERENCES

Burke and Olson, "Preparation of Clone Libraries in Yeast Artificial-Chromosome Vectors" in *Methods in Enzymology*, Vol. 194, "Guide to Yeast Genetics and Molecular Biology", eds. C. Guthrie and G. Fink, Academic Press, Inc., Chap. 17, pp. 251-270 (1991).

Capecchi, "Altering the genome by homologous recombination" *Science* 244:1288-1292 (1989).

Davies et al., "Targeted alterations in yeast artificial chromosomes for inter-species gene transfer", *Nucleic Acids Research*, Vol. 20, No. 11, pp. 2693-2698 (1992).

Dickinson et al., "High frequency gene targeting using insertional vectors", *Human Molecular Genetics*, Vol. 2, No. 8, pp. 1299-1302 (1993).

Duff and Lincoln, "Insertion of a pathogenic mutation into a yeast artificial chromosome containing the human APP gene and expression in ES cells", *Research Advances in Alzheimer's Disease and Related Disorders*, 1995.

Huxley et al., "The human HPRT gene on a yeast artificial chromosome is functional when transferred to mouse cells by cell fusion", *Genomics*, 9:742-750 (1991).

Jakobovits et al., "Germ-line transmission and expression of a human-derived yeast artificial chromosome", *Nature*, Vol. 362, pp. 255-261 (1993).

Lamb et al., "Introduction and expression of the 400 kilobase precursor amyloid protein gene in transgenic mice", *Nature Genetics*, Vol. 5, pp. 22-29 (1993).

Pearson and Choi, *Expression of the human b-amyloid precursor protein gene from a yeast artificial chromosome in transgenic mice*. Proc. Natl. Acad. Sci. USA, 1993. 90:10578-82.

Rothstein, "Targeting, disruption, replacement, and allele rescue: integrative DNA transformation in yeast" in *Methods in Enzmmology*, Vol. 194, "Guide to Yeast Genetics and Molecular Biology", eds. C. Guthrie and G. Fink, Academic Press, Inc., Chap. 19, pp. 281-301 (1991).

Schedl et al., "A yeast artificial chromosome covering the tyrosinase gene confers copy number-dependent expression in transgenic mice", *Nature*, Vol. 362, pp. 258-261 (1993).

Strauss et al., "Germ line transmission of a yeast artificial chromosome spanning the murine $a_1$ (I) collagen locus", *Science*, Vol. 259, pp. 1904-1907 (1993).

Gilboa, E, Eglitis, Mass., Kantoff, PW, Anderson, WF: Transfer and expression of cloned genes using retroviral vectors. BioTechniques 4(6):504-512, 1986.

Cregg JM, Vedvick TS, Raschke WC: Recent Advances in the Expression of Foreign Genes in *Pichia pastoris*, Bio/Technology 11:905-910, 1993

Culver, 1998. Site-Directed recombination for repair of mutations in the human ADA gene. (Abstract) Antisense DNA & RNA based therapeutics, February, 1998, Coronado, Calif.

Huston et al, 1991 "Protein engineering of single-chain Fv analogs and fusion proteins" in Methods in Enzymology (JJ Langone, ed.; Academic Press, New York, N.Y.) 203: 46-88.

Johnson and Bird, 1991 "Construction of single-chain Fvb derivatives of monoclonal antibodies and their production in *Escherichia coli* in Methods in Enzymology (JJ Langone, ed.; Academic Press, New York, N.Y.) 203:88-99.

Mernaugh and Mernaugh, 1995 "An overview of phage-displayed recombinant antibodies" in Molecular Methods In Plant Pathology (RP Singh and US Singh, eds.; CRC Press Inc., Boca Raton, Fla.) pp. 359-365.

Jackson KA, Majka SM, Wang H, Pocius J, Hartley CJ, Majesky MW, Entman ML, Michael LH, Hirschi KK, Goodell Mass. Regeneration of ischemic cardiac muscle and vascular endothelium by adult stem cells. J Clin Invest 2001 June; 107(11):1395-402.

Maltsev Va., Rohwedel J, Hescheler J, Wobus AM: Embryonic stem cells differentiate in vitro into cardiomyocytes representing sinusnodal, artrial and ventricular cell types. *Mechanisms of Development*, 1994; 191:41-50.

Maltsev Va., Wobus AM, Rohwedel J, Bader M, Hescheler J. Cardiomyocytes differentiated in vitro from embryonic stem cells developmentally express cardiac-specific genes and ionic currents. *Circulation Research*, 1994; 75(2):233-244.

Orlic D, Kajstura J, Chimenti S, Jakoniuk I, Anderson SM, Li B, Pickel J, McKay R, Nadal-Ginard B, Bodine DM, Leri A, Anversa P. Bone marrow cells regenerate infracted myocardium. Nature. 2001 Apr. 5; 410(6829):640-1.

Sabbah, HN. Apoptotic cell death in heart failure. Cardiovasc Res. 2000 45:704-712.

Sabbah HN, Stein PD, Kono T, Gheorghiade M, Levine TB, Jafri S, Hawkins ET, Goldstein S. A canine model of chronic heart failure produced by multiple sequential coronary microembolizations. *American Journal of Physiology*. 1991; 260:H1379-84.

Wang JS, Shum-Tim D, Galipeau J, Chedrawy E, Eliopoulos N, Chiu RC. Marrow stromal cells for cellular cardiomyoplasty: feasibility and potential clinical advantages. J Thorac Cardiovasc Surg 2000.

What is claimed is:

1. A method of improving cardiac function of a diseased heart, comprising:
   administering hypoxic bone marrow stem cell (BMSC) preconditioned media into damaged tissue of the heart,
   wherein the hypoxic BMSC preconditioned media is not populated by the bone marrow stem cells that were incubated under hypoxic conditions to produce the hypoxic BMSC preconditioned media; and
   wherein the hypoxic BMSC preconditioned media is therapeutically effective for improving cardiac function by enrichment of the damaged tissue and stimulation of cardiac cell repopulation in the damaged tissue.

2. The method according to claim 1, wherein said administering step includes administering the hypoxic BMSC preconditioned media in a method selected from the group consisting essentially of intravenously, intracoronary, and directly to the heart at a specific location of an injury.

3. A method of improving cardiac function of a diseased heart, comprising:
   preparing a composition consisting of hypoxic bone marrow stem cell (BMSC) preconditioned media that is not populated by the bone marrow stem cells that were incubated under hypoxic conditions to produce the hypoxic BMSC preconditioned media; and
   administering the composition into damaged tissue in the diseased heart to improve cardiac function by enriching the damaged tissue and stimulating repopulation of cardiac cells in the damaged tissue.

4. The method of claim 3, wherein the preparing step comprises:
   incubating bone marrow stem cells (BMSC) in media under 95% nitrogen and 5% carbon dioxide to produce an incubation product; and
   removing the BMSC from the incubation product to produce the hypoxic BMSC preconditioned media.

5. A method of improving cardiac function of a diseased heart, comprising:
   incubating a composition comprising bone marrow stem cells (BMSC) in media under hypoxic conditions;
   harvesting the BMSC from the composition to obtain hypoxic bone marrow stem cell (BMSC) preconditioned media; and
   administering the hypoxic BMSC preconditioned media into damaged tissue in the diseased heart to improve cardiac function by enriching the damaged tissue and stimulating repopulation of cardiac cells in the damaged tissue.

6. The method of claim 5, further comprising, prior to the incubating step:
   isolating the BMSC from harvested marrow; and
   growing the isolated BMSC without differentiation in the media.

7. The method of claim 5, wherein the hypoxic conditions of the incubating step are 95% nitrogen and 5% carbon dioxide.

* * * * *